(12) United States Patent
Albert et al.

(10) Patent No.: US 6,467,479 B1
(45) Date of Patent: Oct. 22, 2002

(54) METHOD AND APPARATUS FOR DELIVERING A MEASURED OF A GAS

(75) Inventors: Mitchell S. Albert; Arvind K. Venkatesh, both of Boston, MA (US); Charles F. Ward, III, Ardmore, PA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 09/415,182

(22) Filed: Oct. 7, 1999

Related U.S. Application Data

(60) Provisional application No. 60/103,659, filed on Oct. 9, 1998.

(51) Int. Cl.[7] .............................................. A61M 16/00
(52) U.S. Cl. ........................... 128/204.23; 128/204.18; 128/204.21; 128/205.24
(58) Field of Search ................. 128/204.18, 204.21, 128/204.23, 205.24, 203.14, 911, 912

(56) References Cited

U.S. PATENT DOCUMENTS

| | | | |
|---|---|---|---|
| 4,015,617 A | | 4/1977 | Connolly ..................... 137/88 |
| 4,267,827 A | | 5/1981 | Rauscher et al. ............ 128/1.1 |
| 4,549,563 A | | 10/1985 | Monnier ...................... 137/100 |
| 4,838,257 A | * | 6/1989 | Hatch ..................... 128/204.18 |
| 4,883,051 A | * | 11/1989 | Westenskow et al. .. 128/204.21 |
| 5,119,810 A | * | 6/1992 | Kiske et al. ............ 128/204.26 |
| 5,183,038 A | | 2/1993 | Hoffman et al. |
| 5,322,057 A | * | 6/1994 | Raabe et al. ........... 128/203.12 |
| 5,507,280 A | * | 4/1996 | Henkin et al. ......... 128/203.12 |
| 6,148,816 A | * | 11/2000 | Heinonen et al. ...... 128/205.24 |

FOREIGN PATENT DOCUMENTS

| | | | |
|---|---|---|---|
| EP | 098 193 | 1/1984 | ........... G05D/11/03 |
| EP | 714 669 | 6/1996 | ........... A61M/16/00 |
| EP | 861 672 | 9/1998 | ........... A61M/16/12 |
| GB | 2 283 179 | 10/1994 | ........... A61M/16/00 |
| WO | WO 98/31282 | 7/1998 | ............ A61B/5/08 |

OTHER PUBLICATIONS

Abstract of AH1 above.
Abstract of AI1 above.

* cited by examiner

*Primary Examiner*—Aaron J. Lewis
*Assistant Examiner*—Mital Patel
(74) *Attorney, Agent, or Firm*—Michael A. Sanzo; Fitch, Even, Tabin & Flannery

(57) ABSTRACT

The present invention uses a ventilator and a series of valves to deliver a special gas into a patient. The present invention finds use in the field of MRI imaging. Attached to the tube extending from the ventilator to the patient is attached a first valve. This valve alternately connects the patient to the ventilator then to a supply of the special gas. Between the first valve and the supply of gas is a second valve, which controls the pressure between the first valve and the second valve caused by the special gas. The supply of special gas is connected to the second valve. A flow regulator controls the rate at which the special gas enters the patient. A computer is also attached to the ventilator and valves to synchronize the opening and closing of the valves and the operation of the ventilator with the patient's respiratory cycles.

13 Claims, 3 Drawing Sheets

METHOD AND APPARATUS FOR DELIVERING A MEASURED OF A GAS

REFERENCE TO EARLIER FILED APPLICATION

This application claims the benefit of U.S. Provisional Application No. 60/103,659, filed Oct. 9, 1998.

BACKGROUND OF THE INVENTION

1. Technical Field

The present invention generally relates to an apparatus for delivering precise amounts of a gas or liquid in a quantifiable manner. In one embodiment of the present invention, the present invention is used to deliver special gas to a patient in a medical setting.

2. Description of the Related Art

It has been recently discovered that injecting certain types of gas into a patients' lungs can greatly improve MRI images taken of the lungs. Hyperpolarized noble gasses such as Xenon 129 and Helium 3 work particularly well for this purpose. However, injecting the correct amount of these gases into a patient's lungs in a magnetic resonance setting has proven difficult.

Therefore, what is needed is a device that can deliver a precise amount of a gas in a medical setting. The device should be compatible for use with a MRI device. Also, it would be advantageous for such a device to be constructed in a simple, reliable manner, using off-the-shelf components. In addition, the design for such a device should be adaptable for use wherever the need to deliver a measured amount of a gas or liquid exists.

SUMMARY OF THE INVENTION

The present invention uses a ventilator and a series of valves to deliver a special gas to a patient. Attached to a tube extending from the ventilator to the patient is a first valve. The valve alternately connects the patient to the ventilator then to a supply of the special gas. Between the first valve and the supply of gas is a second valve, which controls the pressure between the first valve and the second valve caused by the special gas. The supply of special gas is connected to the second valve. A flow regulator controls the rate at which the special gas enters the patient. A controller is also interfaced to the ventilator and valves to synchronize the opening and closing of the valves and the operation of the ventilator with the patient's respiratory cycles. Detection equipment is connected to the controller and is capable of signaling the controller based upon the respiratory cycles of a patient. In this way, the detection equipment can control the position of the first valve in response to a patient's respiratory cycle.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
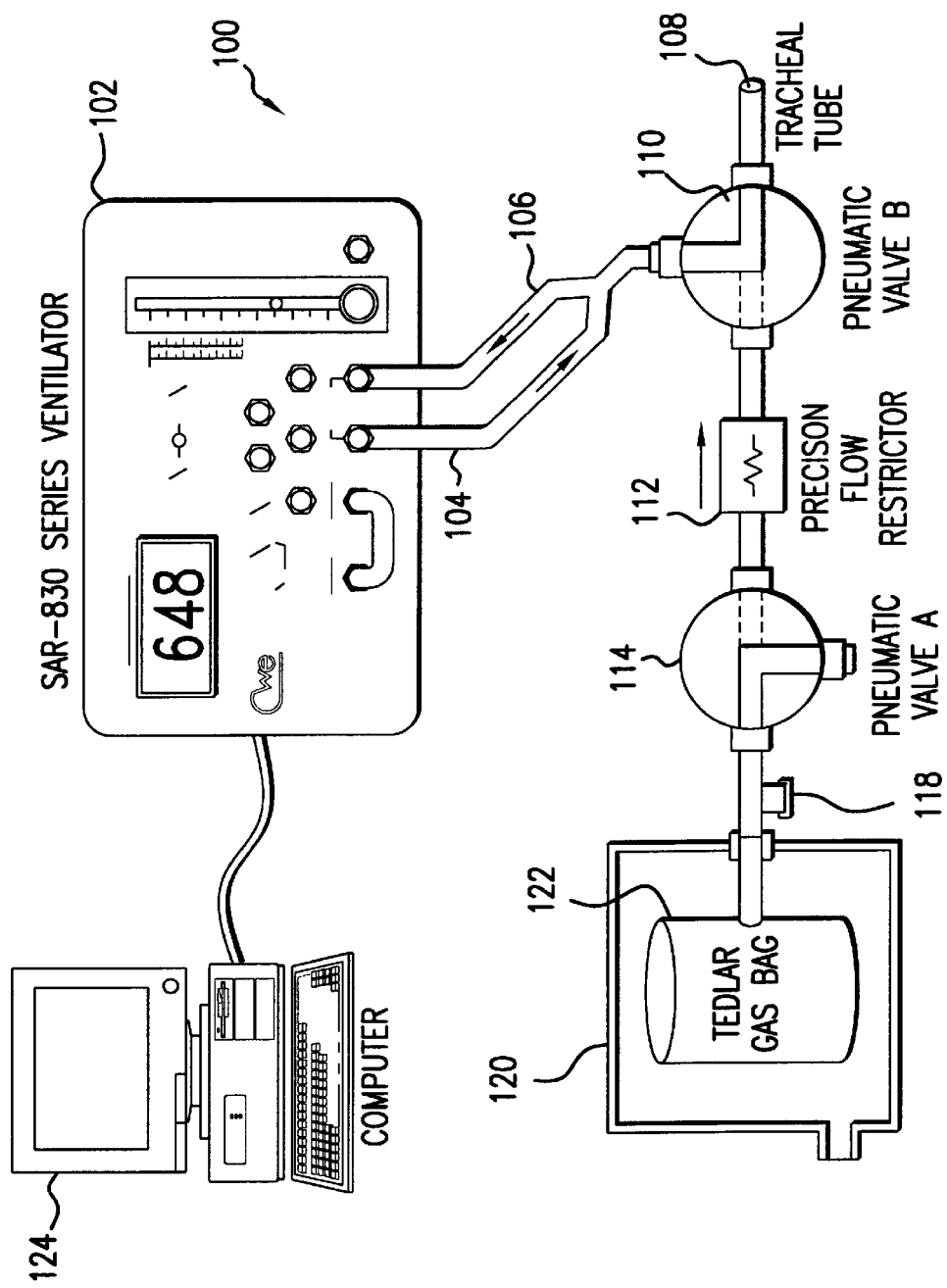
FIG. 1 illustrates a ventilator system according to the present invention.

FIG. 1 illustrates one example of a ventilator system according to the present invention. Ventilator system 100 can be used to deliver specialized gasses or liquids into the lungs, blood vessels, tissue, sinuses, colon, uterine regions, paranasal passages or other void spaces of patients (although the example presented below is restricted to the delivery of a specialized gas to the lungs of a patient). One such application of ventilator system 100 is with MR systems, either imaging (MRI) or spectroscopy (MRS). In one application of ventilator system 100, it has been found that if the lungs of a patient contain a hyperpolarized noble gas, such as certain forms of xenon or helium, when examined by a MRI system, the resulting images show details that are not seen when the lungs are imaged without the hyperpolarized gas (as used herein the term "patient" includes both human and animal subjects, in diseased and in healthy states). Ventilator system 100 can be used to inject a hyperpolarized noble gas into a patient as well as samples such as solids, liquids, and gases. However, as will be explained below, any other gas, or combination of gases, can be injected using ventilator system 100. Further, the components of ventilator system 100 were chosen so that ventilator system 100 could be used inside the bore of a MR or other magnetic device.

As shown in FIG. 1, ventilator system 100 consists of ventilator 102, special gas 122, a system of valves for controlling the injection of special gas 122, and computer 124 for controlling the operation of ventilator 102 and the system of valves. In a preferred embodiment of the present invention, ventilator 102 is a ventilator from CWE Inc. (Ardmore, Pennsylvania), Model SAR-830. However, any standard computer-controllable ventilator can be used with the present invention. Leading from ventilator 102 are airways 104 and 106. As in a standard ventilator, airway 104 supplies air from the ventilator to the patient, while airway 106 withdraws air from the patient and vents it to the atmosphere. Tracheal tube 108 also functions as it normally does in a standard ventilator, as it serves to actually connect the patient to ventilator 102.

Between airways 104 and 106, and tracheal tube 108 is pneumatic valve 110. In a preferred embodiment of the present invention, valve 110 (and pneumatic valve 114) are comprised of zero-dead space, fast-acting valves manufactured by Takasago Electric, located in Midori-Ku, Nagoya, Japan, having part number PMPD-2EM6. Valves 110 and 114 are operated by applying a supply of compressed gas to them. In one embodiment, the control valves which control the operation of valves 110 and 114 may be internal to ventilator 102. In other embodiments, especially if a standard ventilator is used, the control valves which operate valves 110 and 114 will be external to ventilator 102 (in either case, the supply of the compressed gas, the control valves, and the tubes connecting valves 110 and 114 to the control valves are not shown in FIG. 1). In a preferred embodiment of the present invention, compressed helium is used to operate valves 110 and 114, as delays in opening valves 110 and 114 upon receiving a signal to do so are less when helium is used than with compressed air. In a preferred embodiment of the present invention, valves 110 and 114 are constructed of a material that does not alter lines of magnetic flux that surround valves 110 and 114.

In alternative embodiments of the present invention, balloon-type valves can be used in place of the Takasago valves described above. Balloon valves find use when ventilator system 100 is used to supply increased amounts of oxygen and other gasses (including the special gas) to larger animals and humans. These balloon valves operate by closing off a passage when inflated, and by allowing the flow of gas when deflated.

Valve 110 serves to connect tracheal tube 108 to either ventilator 102 or to special gas 122. As referred to in the rest of this Specification, valve 110 is said to be open when it connects ventilator 102 to tracheal tube 108. When closed, valve 110 connects tracheal tube 108 to flow regulator 112 and the other elements shown to the left of pneumatic valve 110 in FIG. 1. When pneumatic valve 110 is open, ventilator 102 is connected to tracheal tube 108 and ventilator 102 functions as does a normal ventilator. When valve 110 is closed, special gas 122 is allowed to flow into the patient via tracheal tube 108.

Special gas 122 is kept inside a Tedlar gas bag, which is a flexible bag that can compress as the special gas is expelled from the bag. The Tedlar bag is kept inside sealed enclosure 120. Enclosure 120 is connected to a compressor or supply of pressurized air (not shown in FIG. 1) to keep a constant pressure within enclosure 120. Keeping a constant pressure within enclosure 120 allows a consistent amount of the special gas to flow into the patient due to flow regulator 112, regardless of the amount of gas within the Tedlar bag. Injection port 118 can be used to refill the Tedlar bag with the special gas when needed.

Valve 114 is used to prevent a build-up of pressure between valve 114 and valve 110, which could result in a sudden release of special gas 122 to the patient when valve 110 is closed. Valve 114 is said to be open when it connects special gas 122 to valve 110. When valve 114 is closed, supply of special gas 122 is connected to a portion of valve 114 which has been plugged. During operation, valve 110 will open approximately 10 milliseconds before valve 114 opens to prevent any of special gas 122 from flowing back into ventilator 102. Flow regulator 112 is used to supply special gas 122 to the patient at a known rate. This type of operation occurs because special gas 122 is delivered to flow regulator 112 at a constant pressure.

Figure 2:
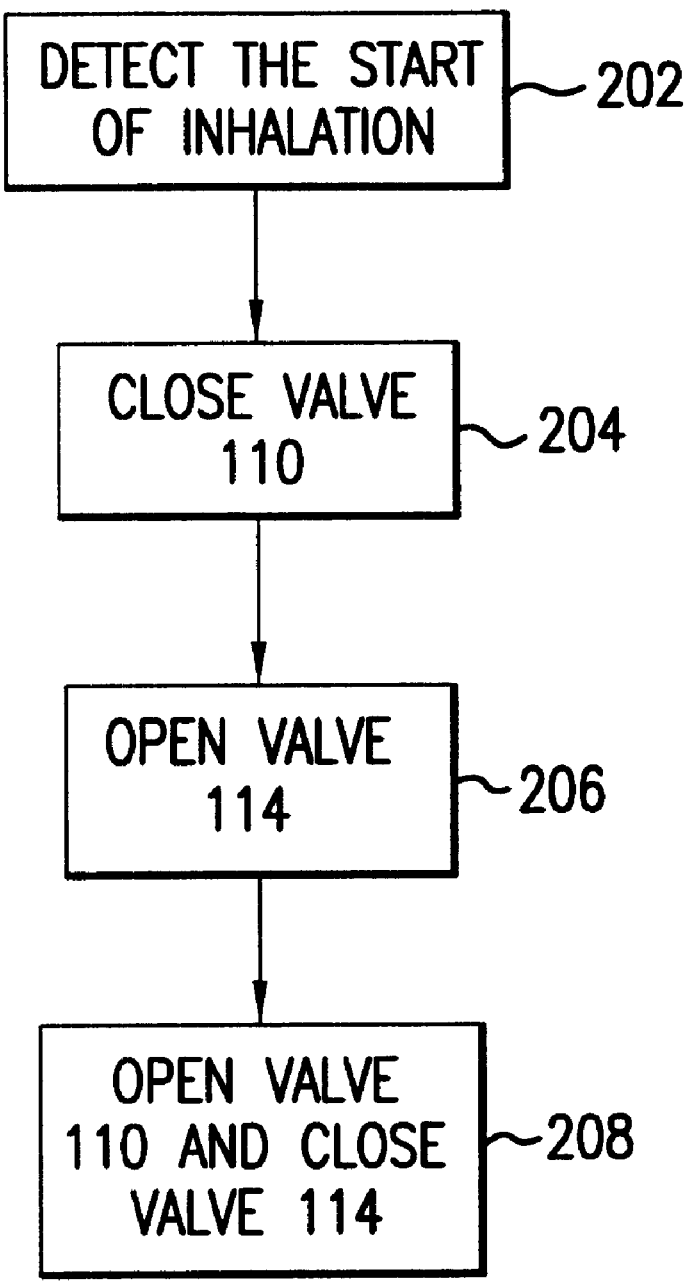
FIG. 2 is a flowchart illustrating a method according to the present invention.

FIG. 2 is a flowchart which illustrates how computer 124 operates ventilator 102 and valves 110 and 114. Computer 124 is connected to ventilator 102 and to the equipment which operates valves 110 and 114. Also, computer 124 receives information concerning the patient's respiratory cycles from devices and/or equipment as known in the art. A program executes on computer 124 which synchronizes the operation of ventilator 102 and valves 110 and 114. In operation, computer 124 detects the start of inhalation of the patient (202). This point of the respiratory cycle has been shown to be the optimal time to inject special gas 122 into the patient. Once the inhalation process is detected, computer 124 closes valve 110, thereby disconnecting ventilator 102 from the patient (204). After a short period of time (~10 milliseconds), computer 124 opens valve 114, thereby allowing the special gas to flow into the patient (206). How long computer 124 allows the special gas to flow into the patient depends on many factors. The size of the patient, the amount of special gas that is needed in the patient for optimal imaging, the flow rate of the gas into the patient as determined by flow regulator 112, and the type of special gas used all must be considered in determining how long to keep valve 110 closed and valve 114 open. After enough of the special gas has been injected into the patient, valve 114 is opened and valve 110 closed (208), thereby reconnecting ventilator 102 to the patient.

Although the present invention is shown with only valves 110 and 114, other valves can be connected to ventilator system 100, shown in FIG. 1, to deliver other types of special gas along with the special gas shown in FIG. 1. In these alternate embodiments, the other valves are simply connected to the computer and the airway leading to the tracheal tube, as described above.

For example, a second supply of gas attached to a pneumatic valve and precision flow regulator can be connected to ventilator system 100 by attaching the new precision flow regulator in parallel with precision flow regulator 112 and pneumatic valve 110, as shown in FIG. 1 (i.e., the conduit supplying the second supply of gas would join the conduit between flow regulator 112 and valve 110). In turn, the supply of gas would be connected to the new pneumatic valve, which would be attached to the new precision flow regulator. In addition, the new pneumatic valve would be attached to the computer system that controls valves 112 and 110 so that the release of the second supply of gas could be coordinated with the rest of ventilator system 100. Being able to deliver special gas from two supplies would allow one container of special gas to contain a gas which enhances the images generated in an MRI procedure, while the second supply of special gas could contain a stimulus-producing agent (e.g., aerosolized drugs) to treat the patient.

Many variations of the ventilator system described above can be created for a particular situation. For example, the ventilator shown in FIG. 1 can be implemented by almost any type of ventilator or other source of pressurized gas. In addition, the special gas does not have to be xenon or helium. Radioactive gasses, aerosols, nebulized sprays, macro molecular aggregates, and suspended particles (solid particles suspended or mixed in a gas or liquid are, for the purposes of this specification and claims, considered to be either a gas or liquid) can be used, again, depending upon the application of the ventilator system.

Expanding further, the ventilator system described above can be adapted to any number of situations where there is a need to deliver a measured amount of gas or liquid in a controlled manner. For example, in certain applications, a compressor, fan, or other supply of pressurized gas can be used in place of the ventilator. Also, a variety of valves can be used. In some situations, the valves themselves can regulate the amount of gas or liquid dispensed, in conjunction with or in place of the flow regulator. Further, additional controls can regulate the pressure at which the special gas or liquid is transferred to the series of valves. Also, a dedicated controller can be used in place of a computer to control the valves.

Figure 3:
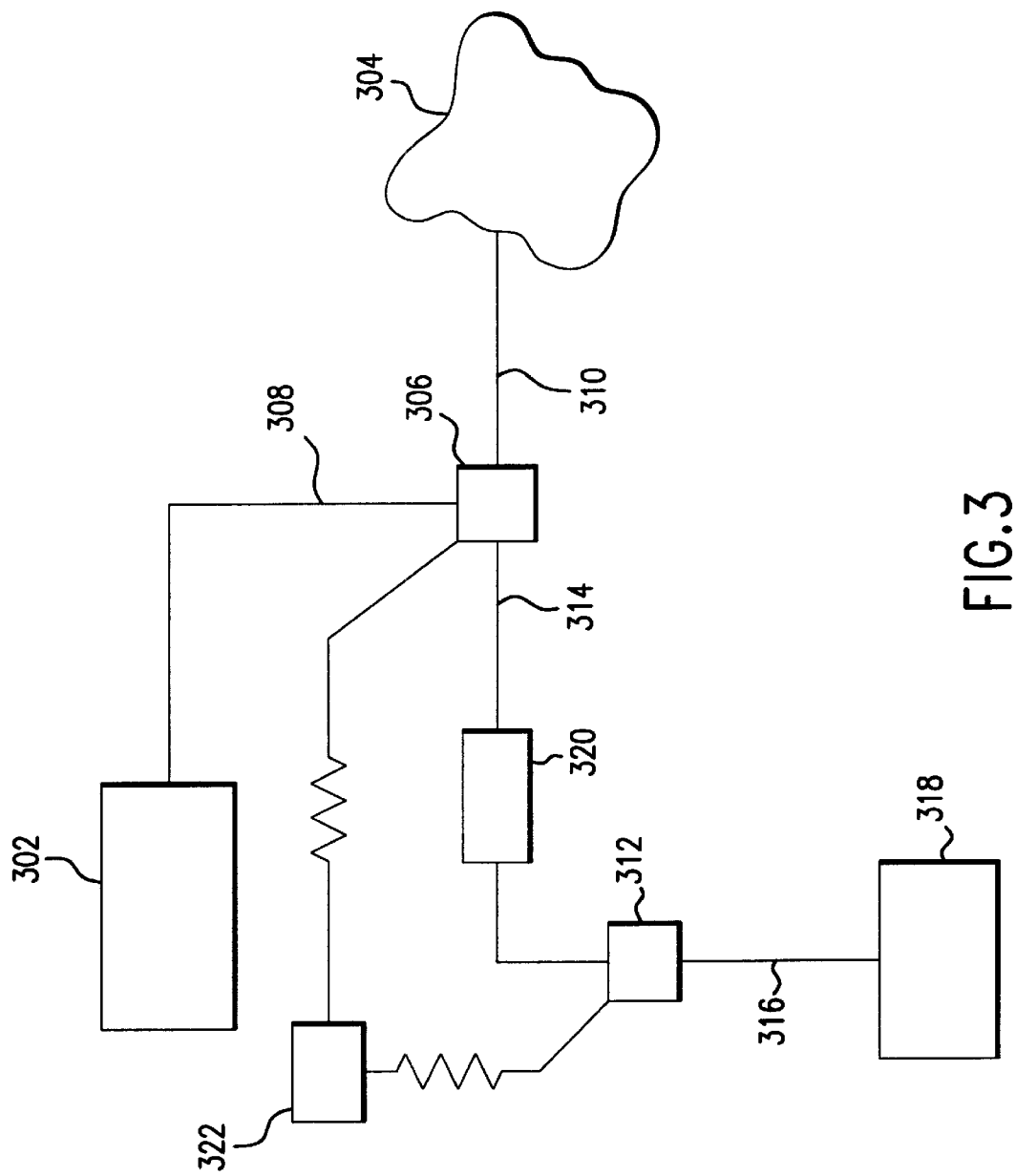
FIG. 3 illustrates a more general purpose material delivery system.

FIG. 3 illustrates a more general purpose version of the ventilator shown in FIG. 1. Container 302 contains an amount of material that can be delivered to region of interest 304. Container 302 is connected to a valve 306 by conduit 308. Leading away from valve 306 is conduit 310. Conduit 310 alternately delivers materials from containers 302 and 318 to region of interest 304. Valve 306 is also connected to valve 312 by conduit 314. Attached to valve 312 is container 318, which contains the special material to be delivered to region of interest 304. Container 318 is attached to valve 312 by conduit 316. The amount of special material delivered to region of interest 304 is controlled, at least partially, by flow regulator 320, located on conduit 314. Finally, controller 322 regulates the opening and closing of valves 306 and 312 to accomplish the delivery of the special material, along with the material contained in container 302, to the region of interest. The materials within containers 302 and 318 are normally under pressure and flow when the appropriate valves are open (or closed). However, these containers can be attached to compressors or fans, or can simply be comprised of a compressor or fan (or, as in the case of the example shown in FIG. 1, a ventilator). Likewise, as discussed above, additional containers of material and valves can be integrated into the system shown in FIG. 3 in order to deliver more than two different types of material to a region of interest.

While the invention has been particularly shown and described with reference to a preferred embodiment, it will be understood by those skilled in the art that various changes in form and detail may be made therein without departing from the spirit and scope of the invention.

What is claimed:

1. a combination of a special gas and a device for delivering the special gas to a patient, said combination comprising:
   (a) a ventilator comprising a tube for gas flow suitable for connecting said ventilator to a patient;
   (b) a first valve located on said tube for gas flow and connected to a container of said special gas, wherein said first valve may alternate position to open said tube for gas flow to either said ventilator or to said container of special gas;
   (c) a controller connected to said ventilator and said first valve, wherein said controller controls the position of first valve;
   (d) detection equipment connected to said controller, wherein said detection equipment is capable of signaling respiratory cycles of a patient and controlling the position of said first valve in response to said respiratory cycles;
   (e) a second valve connected between said container of special gas and said first valve, wherein said second valve allows gas to flow to said first valve after said first valve connects to the special gas.

2. The combination of claim 1, further comprising a regulator located between said first valve and said second valve for metering the flow of said special gas.

3. The combination of claim 1, wherein said special gas is Xenon.

4. The composition of matter of claim 1, wherein said first valve and said second valve are controlled by a supply of compressed helium.

5. The combination of claim 1, wherein said special gas is a stimulus producing agent.

6. A method of delivering a special gas to a patient, comprising;
   (a) connecting said patient to the gas flow tube of the combination of claim 1;
   (b) sensing the respiratory cycles of said patient using said detection equipment;
   (c) controlling the position of said first valve based upon said respiratory cycles;
   (d) connecting said patient to a container of said special gas by changing the position of said first valve;
   (e) delivering said special gas to said patient.

7. The method of claim 6, further comprising metering the flow of said special gas to said patient using a flow regulator.

8. The method of claim 6, wherein said special gas is Xenon.

9. The method of claim 6, wherein said first valve and said second valve are controlled by a supply of compressed helium.

10. The method of claim 6, wherein said special gas is a stimulus producing agent.

11. a combination of a device for delivering a measured amount of a special material to a region of interest, a special material and a first material, said combination comprising:
   (a) a container of said first material;
   (b) a first conduit having a first and second end, wherein the first end of the first conduit is connected to the container of the first material;
   (c) a first valve having a first opening, a second opening, and a third opening, wherein the second end of the first conduit is connected to the first opening of the first valve;
   (d) a supply conduit having a first and second end, wherein the first end of the first conduit is connected to the second opening of the first valve and the second end of the supply conduit is located in the region of interest;
   (e) a second valve having a first opening and a second opening;
   (f) a second conduit having a first and second end, wherein the first end of the second conduit is attached to the first opening of the second valve and the second end of the second conduit is attached to the third opening of the first valve;
   (g) a flow regulator attached to the second conduit between the first and second ends of the second conduit;
   (h) a second supply unit for delivering the special material;
   (i) a third conduit having a first and second end, wherein the first end of the third conduit is attached to the container of the special material and the second end of the third conduit is attached to the second opening of the second valve;
   (j) a controller for operating the first and second valves, wherein the controller alternately places the first valve into an open state which blocks the flow of the first material through the first valve and allows the special material to flow from the second conduit through the third opening of the first valve and out of the second opening of the first valve, and a closed state which blocks the flow of the special material through the first valve and allows the first material to flow from the first conduit through the first opening of the first valve and out of the second opening of the first valve; and wherein the controller alternately places the second valve in a closed state which blocks the flow of the special material through the second valve and an open state which allows the special material to flow from the third conduit through the second opening of the second valve and out of the first opening of the second valve.

12. The combination of claim 11, wherein the container of the first material comprises any one of: a compressor, a ventilator, and a fan.

13. The combination of claim 11, wherein the first material is either a gas or liquid and the special material is either a gas or liquid.

* * * * *

UNITED STATES PATENT AND TRADEMARK OFFICE
CERTIFICATE OF CORRECTION

PATENT NO. : 6,467,479 B1  
APPLICATION NO. : 09/415182  
DATED : October 22, 2002  
INVENTOR(S) : Albert et al.

Page 1 of 1

It is certified that error appears in the above-identified patent and that said Letters Patent is hereby corrected as shown below:

On the cover page, item (54) and in column 1, lines 1-2, the title should read as follows:

-- METHOD AND APPARATUS FOR DELIVERING A MEASURED AMOUNT OF A GAS --

In column 1, after the section entitled "REFERENCE TO EARLIER FILED APPLICATION" and before the heading "BACKGROUND OF THE INVENTION" that appears on line 9, a paragraph should be added citing Government funding. The added paragraph should read as follows:

-- Statement of Government Support
  This invention was made with Government support under Grant No. BES9617342 awarded by the National Science Foundation. The U.S. Government therefore has certain rights in the invention. --

Signed and Sealed this

Eighteenth Day of August, 2009

David J. Kappos
*Director of the United States Patent and Trademark Office*